(12) United States Patent
Hinchliffe

(10) Patent No.: US 6,314,805 B1
(45) Date of Patent: Nov. 13, 2001

(54) YARN QUALITY MONITORING

(75) Inventor: Malcolm Geoffrey Hinchliffe, Macclesfield (GB)

(73) Assignee: Merlin Partnership (GB)

( * ) Notice: Subject to any disclaimer, the term of this patent is extended or adjusted under 35 U.S.C. 154(b) by 0 days.

(21) Appl. No.: 09/565,057

(22) Filed: May 3, 2000

(30) Foreign Application Priority Data

May 6, 1999 (GB) .................................................. 9910331

(51) Int. Cl.[7] .............................................. G01L 5/04
(52) U.S. Cl. .............................................. 73/160
(58) Field of Search .......................... 73/826, 828, 160, 73/579

(56) References Cited

U.S. PATENT DOCUMENTS

| | | | |
|---|---|---|---|
| 4,195,345 | * 3/1980 | Artzt et al. | 364/470.1 |
| 4,880,175 | * 11/1989 | Yamauchi et al. | 242/412.1 |
| 5,164,710 | * 11/1992 | Anderegg et al. | 340/677 |
| 5,577,676 | * 11/1996 | Berger et al. | 242/18.1 |
| 5,954,289 | * 9/1999 | Hermanns et al. | 242/477.8 |

* cited by examiner

*Primary Examiner*—Max Noori
(74) *Attorney, Agent, or Firm*—Schwegman, Lundberg, Woessner & Kluth, P.A.

(57) ABSTRACT

A method of monitoring on-line the initial modulus of a spun and at least partially drawn textile yarn is provided. The method consists of forwarding the yarn from a forwarding point to a package, winding the yarn on the package whilst traversing the yarn adjacent the package at a periodically disturbed speed, and continuously measuring the short term variation in yarn tension due to the change in yarn path length between the forwarding point and the package. An alarm is initiated if the sampled data is equals predetermined limits. The initial modulus of the yarn is calculated from the amplitude of the tension variations.

20 Claims, 1 Drawing Sheet

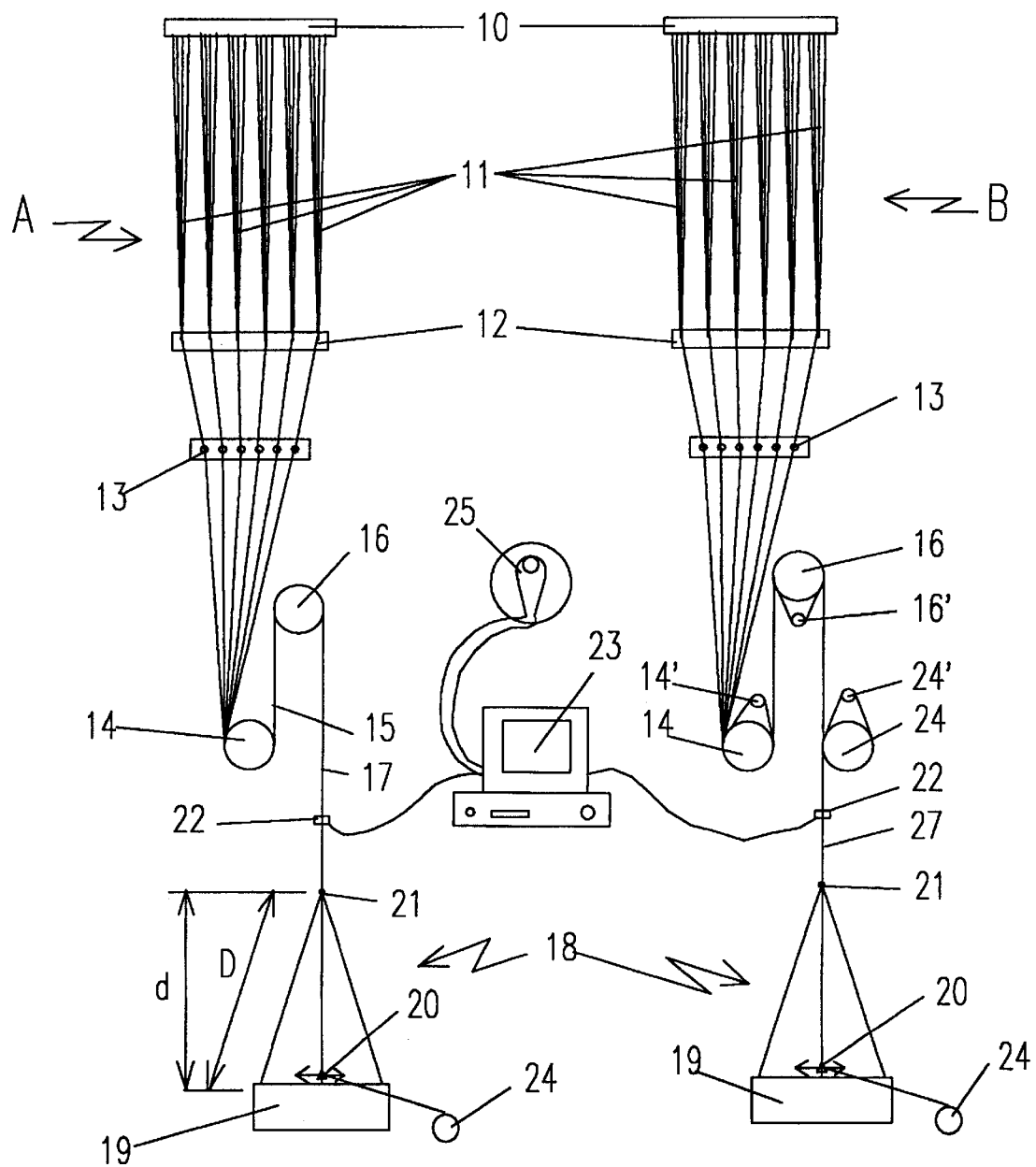

YARN QUALITY MONITORING

FIELD OF THE INVENTION

This invention relates to the monitoring of the properties of a textile yarn on formation after spinning, in particular those properties relating to the morphological aspects that affect the perceived quality of the spun yarn.

BACKGROUND OF THE INVENTION

To date a number of on-line monitoring methods have evaluated quality in partially oriented yarns (POY) or fully drawn yarns (FDY) yarn spinning processes. One such method is that of the on-line measurement of the denier regularity. Another method is that of tension measurement between the spinneret and the first godet. Although in many processes there may be a reasonably stable tension in this zone with a minimum of disturbing factors, nevertheless in more and more processes oil dispersing air jets are fitted in this zone, creating a source of significant tension variations and disturbance. The main component of force in this zone is a variable air drag on the filaments prior to them being formed into a yarn at the first contact point—the oil applicator guide, but there are other influences that reduce the value of this tension measurement as indicative of the morphological aspects of the spun yarn. These include the friction of the filament bundle with the oil and guide surfaces, the effect of the air jets if fitted and the draw force of the yarn. As an alternative method, the yarn tension may be measured in other zones, for example between the first and second godet and between the second godet and the take-up, but these arrangements have also failed to provide methods of obtaining useful information due to the large tension variations in these areas. Between the godets it is usual to fit air jets which cause substantial tension variations. After the godets the tension is cyclically variable because of the change in yarn length due to the traversing of the yarn as it is forwarded onto the package, the tension variation frequency being twice that of the traverse. Typically a 0.5 to 1.0% yarn path length change occurs during the winding process. In addition, to prevent patterning during the winding process, the traversing of the yarn is usually subjected to a periodic disturbance, which causes a variation in the change of yarn path length. Because of the above described problems, to date none of the above described methods has been commercially successful.

It is now well known that a key parameter indicative of the quality of POY and FDY is the "draw force". This is the tensile force at which the extension of the yarn increases considerably for substantially no increase in that force. The draw force, to which the initial modulus of the POY or FDY is directly related, is a very small factor influencing the tension in the yarn in the zone prior to the first godet, and is swamped by the accepted variations from the other sources. As a consequence, it has been effectively impossible to obtain useful information about draw force from a tension measurement in this zone. Hence to date, such a measurement has been made under laboratory conditions as a routine quality control test, but in such a way that only a very small sample from a small percentage of the packages produced can be tested in practice. In consequence there has been a requirement for a method of monitoring this parameter, or a closely related parameter, on-line so that the quality of 100% of all yarn produced can be evaluated.

SUMMARY OF THE INVENTION

The invention provides a method of monitoring on-line the initial modulus of a spun and at least partially drawn textile yarn, comprising forwarding the yarn from a forwarding point to a package, winding the yarn on the package whilst traversing the yarn adjacent the package, and continuously measuring the short term variation in yarn tension due to the change in yarn path length between the forwarding point and the package.

The method may comprise determining the amplitude of the tension variations in the yarn, and may comprise calculating the initial modulus of the yarn from that amplitude. The yarn may be traversed at a predetermined traversing frequency, in which case the tension may be measured using a tension sensor having a natural frequency response above the traversing frequency. The sensor frequency response may be substantially six times the traversing frequency, and may be in the range 15 to 75 cycles/sec, for example substantially 450 Hz. The signals from the sensor may be sampled at frequency in the range 1000 to 5000 Hz, and may be sampled using a distributed electronics to provide sampled data. The signals from the sensor may be subjected to noise filtering.

The speed of traversing of the yarn may be periodically disturbed, in which case the speed variation may be cycled over a fixed time period or alternatively over a variable time period. The frequency of the traverse may be monitored, and may be averaged over the time cycle of the disturbance.

The sampled data may be compared with predetermined limits, and in the event that the data is of a magnitude at least equal to a limit, an alarm may be initiated. The alarm may be initiated at the location of measuring the yarn tension, or at a computer remote from the location of measuring the yarn tension.

BRIEF DESCRIPTION OF THE DRAWING

The invention will now be further described with reference to the accompanying drawing, in the single FIGURE of which there is shown on the left a production line for POY, and on the right a production line for FDY

DESCRIPTION OF THE PREFERRED EMBODIMENTS

Referring now to the production line A for POY yarn, having a spinneret 10 from which filaments 11 are extruded. Spin finish oil is applied to the filaments 11 by an oil applicator 12, and the regularity of the oil application is improved by oil dispersion jets 13. The filaments are brought together at a first godet 14, and the resulting yarn 15 is drawn to a desired extent between that first godet 14 and a second godet 16. The partially drawn yarn 17 is the fed to a take up zone 18 to be wound on a package 19 using a traverse guide 20 which reciprocates as shown along a path parallel with the axis of the package 19 at a predetermined frequency which may be in the range of 15 to 75 cycles per second. Because of this the path length of the yarn between a forwarding point 21 and the package varies cyclically, the distance D from the forwarding point 21 to the ends of the package 19 being in the region of 0.5 to 1.0% longer than the distance d between the forwarding point 21 and the centre of the package 19. This path length change creates a change in the tension in the yarn 17 and hence a stretching of the yarn 17, which also varies cyclically at twice the traverse speed, i.e. in the range 30 to 150 Hz. The rotational speed of the second godet is measured to give the speed of forwarding the yarn 17 to the package 19. The stretch in the yarn 17 is the distance D-d, and this is effected on a yarn length of sum of the distance d and the amount of yarn 17 fed into this zone during ¼ of a traverse cycle. With this stretch per unit length expressed as a percentage, the modulus of the yarn 17 expressed in grams/% is calculated from the change in tension during a cycle divided by the percentage stretch. The yarn tension is measured by a tension sensor 22, and hence the change in tension during a cycle may be determined. The sensor 22 has a higher frequency response than the frequency of the tension variation, and such frequency response may be in the region of 450 Hz, i.e. some six times the traverse frequency. The signal from the sensor 22 are sampled by a computer device 23, which may be located adjacent the sensor 22 or may be at some remote location (shown as common to FIG. 1 in this case). The signals from the sensor 22 are sampled at frequency in the range 1000 to 5000 Hz, and are sampled using a distributed electronics to provide sampled data. The signals may be subjected to noise filtering by the computer device 23 as required. The speed of traverse guide 20 is periodically disturbed by a disturbance mechanism 24, and this speed variation may be cycled over fixed or variable time periods. In these cases the arrangement compensates for the variation in yarn path length due to the effects of the disturbance mechanism 24 by the frequency of the traverse guide 20 being monitored by a position sensor 25 which also sends signals to the computer device 23, or such signals are used to average the traverse speed over the time cycle of the disturbance.

The sampled data may be compared with predetermined limits programmed into the computer device 23. In the event that the data is of a magnitude at least equal to a limit, an alarm 25 may be initiated. The alarm 25 may be initiated at the location of the yarn tension sensor 22, or may be initiated at the computer device 23 remote from such location.

The production line B for FDY yarn, has many of the features described in relation to the POY production line A, and corresponding features are identified by the same numerals. In this case however the first godet 14 of the POY production line A is replaced by a first godet 14 and a separator roll 14'. Similarly the second godet 16 of the POY production line A is replaced by a second godet 16 and second separator roll 16'. This arrangement facilitates drawing of the filaments 11 to a much greater extent than in the case of the POY 17. A third godet 24 and separator roll 24'may also be provided so that the yarn 27 is fully drawn. In all other respects the production and quality monitoring of the FDY 27 is the same as that for POY 17.

By means of the invention a method is provided for the on-line monitoring of the draw force of the spun POY or FDY yarn by taking a different approach to tension measurement from the methods currently used. The tension measurement is made using a tension sensor having a frequency response some three times that of the sensors currently used in the methods adopted to date in the textile industry. The determination of the initial modulus of the yarn, which is directly related to the draw force as measured in a laboratory, provides the required on-line quality control of the yarn.

What is claimed is:

1. A method of monitoring on-line an initial modulus of a spun and at least partially drawn textile yarn, comprising forwarding the yarn from a forwarding point along a yarn path to a package, winding the yarn on the package whilst traversing the yarn adjacent the package, continuously measuring short term variation in yarn tension due to a change in length of the yarn path between the forwarding point and the package, and calculating the initial modulus of the yarn from the tension measurements.

2. A method according to claim 1, comprising determining the amplitude of the tension variations in the yarn.

3. A method according to claim 2, comprising calculating the initial modulus of the yarn from that amplitude.

4. A method according to claim 1, wherein the yarn is traversed at a predetermined traversing frequency.

5. A method according to claim 4, comprising measuring the tension at a location using a tension sensor having a natural frequency response above the traversing frequency.

6. A method according to claim 5, wherein the sensor has a frequency response that is substantially six times the traversing frequency.

7. A method according to claim 5, wherein the traversing frequency is in the range 15 to 75 cycles/sec.

8. A method according to claim 5, wherein the sensor frequency response is substantially 450 Hz.

9. A method according to claim 5, wherein the sensor provides signals and the signals are sampled at frequency in the range 1000 to 5000 Hz.

10. A method according to claim 5, wherein the sensor provides signals and the signals are sampled using a distributed electronics to provide sampled data.

11. A method according to claim 5, wherein the sensor provides signals and the signals are subjected to noise filtering.

12. A method according to claim 1, wherein the yarn is traversed at a speed that is periodically disturbed.

13. A method according to claim 12, wherein the speed of traversing the yarn is cycled over a fixed time period.

14. A method according to claim 12, wherein the speed of traversing the yarn is cycled over a variable time period.

15. A method according to claim 12, wherein the yarn is traversed at a frequency that is monitored.

16. A method according to claim 12, wherein the yarn is traversed at a frequency that is averaged over the time cycle of the disturbance.

17. A method according to claim 10, wherein the sampled data is compared with predetermined limits.

18. A method according to claim 17, wherein in the event that the data is of a magnitude at least equal to a limit, an alarm is initiated.

19. A method according to claim 18, wherein the alarm is initiated at the location of measuring the yarn tension.

20. A method according to claim 18, wherein a computer is located remote from the location of measuring the yarn tension and the alarm is initiated at the computer.

* * * * *